United States Patent [19]
Nikiforov et al.

[11] Patent Number: 5,679,524
[45] Date of Patent: Oct. 21, 1997

[54] LIGASE/POLYMERASE MEDIATED GENETIC BIT ANALYSIS OF SINGLE NUCLEOTIDE POLYMORPHISMS AND ITS USE IN GENETIC ANALYSIS

[75] Inventors: Theo Nikiforov, Baltimore, Md.; Jonathan Karn, Little Shelord, United Kingdom; Philip Goelet, Cockeysville, Md.

[73] Assignee: Molecular Tool, Inc., Baltimore, Md.

[21] Appl. No.: 694,835

[22] Filed: Aug. 9, 1996

Related U.S. Application Data

[63] Continuation of Ser. No. 192,631, Feb. 7, 1994, abandoned.
[51] Int. Cl.⁶ .................................................. C12Q 1/68
[52] U.S. Cl. ............................. 435/6; 435/5; 435/91.1; 435/91.2; 435/810; 436/501; 536/24.1; 536/24.3; 536/24.31; 536/24.32; 536/24.33; 935/77; 935/78
[58] Field of Search ........................ 435/5, 6, 91.1, 435/91.2, 810; 436/501; 536/24.1, 24.3–33; 935/77, 78

[56] References Cited

U.S. PATENT DOCUMENTS

| | | | |
|---|---|---|---|
| 4,656,127 | 4/1987 | Mundy | 435/6 |
| 4,683,194 | 7/1987 | Saiki et al. | 435/6 |
| 4,683,202 | 7/1987 | Mullis | 435/91 |
| 5,175,082 | 12/1992 | Jeffreys | 435/6 |
| 5,185,243 | 2/1993 | Ullman et al. | 435/6 |
| 5,427,930 | 6/1995 | Birkenmeyer et al. | 435/91.52 |

FOREIGN PATENT DOCUMENTS

| | | | |
|---|---|---|---|
| 0246864 | 11/1987 | European Pat. Off. | |
| 0370719 | 5/1990 | European Pat. Off. | C12Q 1/68 |
| 0439182 | 7/1991 | European Pat. Off. | C12Q 1/68 |
| 2135774 | 9/1984 | United Kingdom | C12Q 1/68 |
| WO90/11369 | 10/1990 | WIPO | C12Q 1/68 |
| WO90/13668 | 11/1990 | WIPO | C12Q 1/68 |
| WO91/02087 | 2/1991 | WIPO | C12Q 1/68 |
| WO92/15712 | 9/1992 | WIPO | C12Q 1/68 |

OTHER PUBLICATIONS

Matthews et al. (1988) Analytical Chem., vol. 169, pp. 1–25.
Jeffreys. A.J. et al, "DNA Fingerprints and Segregation Analysis of Multiple Markers in Human Pedigrees", *Amer. J. Hum. Genet.* 39:11–24 (1986).
Mullis, K.B., "The Unusual Origin of the Polymerase Chain Reaction," *Scientific American* Apr. 1990.
Saiki, R.K. et al., "A Novel Method for the Detection of Polymorphic Restriction Sites by Cleavage of Oligonucleotide Probes: Application to Sickle-Cell Anemia," *Bio/Technol.* 3:1008–1012 (1985).
Belle White, M. et al., "Detecting Single Base Substitutions as Heteroduplex Polymorphisms," *Genomics* 12:301–306 (1992).
Wu, D.Y. et al., "The Ligation Amplification Reaction (LAR)—Amplification of Specific DNA Sequences Using Sequential Rounds of Template-Dependent Ligation," *Genomics* 4:560–569 (1989).
Nickerson, D.A. et al., "Automated DNA Diagnostics Using an ELISA-based Oligonucleotide Ligation Assay," *Proc. Natl. Acad. Sci. (U.S.A.)* 87:8923–8927 (1990).

(List continued on next page.)

*Primary Examiner*—Ardin H. Marschel
*Attorney, Agent, or Firm*—Howrey & Simon; Jeffrey I. Auerbach

[57] ABSTRACT

A method is provided for determining the identity of a nucleotide at a preselected site in a nucleic acid molecule. The method involves the incorporation of a nucleoside triphosphate that is complementary to the nucleotide present at the preselected site onto the terminus of a primer molecule, and their subsequent ligation to a second oligonucleotide. The reaction is monitored by detecting a specific label attached to the reaction's solid phase or by detection in solution.

24 Claims, 4 Drawing Sheets

OTHER PUBLICATIONS

Kwoh, D.Y. et al., "Transcription–Based Amplification System and Detection of Amplified Human Immunodeficiency Virus Type 1 with a Bead–Based Sandwich Hybridization Format," *Proc. Natl. Acad. Sci. (U.S.A.)* 86:1173–1177 (1989).

Frohman, M.A. et al., "Rapid Production of Full–Length cDNAs from Rare Transcripts: Amplification Using a Single Gene–Specific Oligonucleotide Primer," *Proc. Natl. Acad. Sci. (U.S.A.)* 85:8998–9002 (1988).

Walker, G.T. et al., "Isothermal in vitro Amplification of DNA by a restriction enzyme/DNA polymerase System," *Proc. Natl. Acad. Sci. (U.S.A.)* 89:392–396 (1992).

Landegren, U. et al., "Oligonucleotide Ligation Assay," Science 241:1077–1080 (1988).

Walker, G.T. et al., "Isothermal in vitro Aplification of DNA byction enzyme/DNA polymerase System," *Proc. Natl. Acad. Sci. (U.S.A.)* 89:392–396 (1992).

Mathews, et al., *Analytical Chem.* 69:1–25(1988).

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Equus caballus ( x i ) SEQUENCE DESCRIPTION: SEQ ID NO:1:

GTGGAGATCA CAGACTGAAA TATTG    2 5

( 2 ) INFORMATION FOR SEQ ID NO:2:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Equus caballus ( x i ) SEQUENCE DESCRIPTION: SEQ ID NO:2:

AGTATAATAA TCACAGTATG TTAGC     25

( 2 ) INFORMATION FOR SEQ ID NO:3:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Equus caballus ( x i ) SEQUENCE DESCRIPTION: SEQ ID NO:3:

ACCTTCAAAA CTCAACTCAG CTCTT     25

( 2 ) INFORMATION FOR SEQ ID NO:4:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Equus caballus ( x i ) SEQUENCE DESCRIPTION: SEQ ID NO:4:

TTTACCAATG AGAAGGACAT CTAAG     25

( 2 ) INFORMATION FOR SEQ ID NO:5:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Equus caballus ( x i ) SEQUENCE DESCRIPTION: SEQ ID NO:5:

TTCTCCCAGT GGCACAGTAA AATTG 25

( 2 ) INFORMATION FOR SEQ ID NO:6:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Equus caballus ( x i ) SEQUENCE DESCRIPTION: SEQ ID NO:6:

GCTTCTACAT TCATTTCTT GTTCT 25

( 2 ) INFORMATION FOR SEQ ID NO:7:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Equus caballus ( x i ) SEQUENCE DESCRIPTION: SEQ ID NO:7:

AATTTTACTG TGCCACTGGG AGAACAGAAC AAGAAAATGA ATGTAGAAGC 50

( 2 ) INFORMATION FOR SEQ ID NO:8:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Equus caballus ( x i ) SEQUENCE DESCRIPTION: SEQ ID NO:8:

CTCCCAGTGG CACAGTAAAA TTGGT 25

( 2 ) INFORMATION FOR SEQ ID NO:9:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear

```
        ( i i ) MOLECULE TYPE: DNA (genomic)

( i i i ) HYPOTHETICAL: NO ( i v ) ANTI-SENSE: NO ( v i ) ORIGINAL SOURCE:
                ( A ) ORGANISM: Equus caballus ( x i ) SEQUENCE DESCRIPTION: SEQ ID NO:9:

TTCTACATTC ATTTTCTTGT TCTGT                                                                        2 5

( 2 ) INFORMATION FOR SEQ ID NO:10:

( i ) SEQUENCE CHARACTERISTICS:
                ( A ) LENGTH: 56 base pairs
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                ( A ) ORGANISM: Equus caballus ( x i ) SEQUENCE DESCRIPTION: SEQ ID NO:10:

ACCAATTTTA CTGTGCCACT GGGAGAACAG AACAAGAAAA TGAATGTTAG AAGCAT                                      5 6
```

LIGASE/POLYMERASE MEDIATED GENETIC BIT ANALYSIS OF SINGLE NUCLEOTIDE POLYMORPHISMS AND ITS USE IN GENETIC ANALYSIS

CROSS REFERENCE TO RELATED APPLICATIONS

This application is a continuation of U.S. patent application Ser. No. 08/192,631, filed Feb. 27, 1994, now abandoned.

FIELD OF THE INVENTION

The present invention is in the field of recombinant DNA technology. More specifically, the invention is directed to a ligase/polymerase-mediated method for determining the identity of the nucleotide that is present at a particular site, such as a single nucleotide polymorphic site, in the genome of an animal. The invention further concerns the use of such determinations to analyze identity, ancestry or genetic traits.

BACKGROUND OF THE INVENTION

I. The Determination of The Nucleotide Present at a Polymorphic Site

The genomes of viruses, bacteria, plants and animals naturally undergo spontaneous mutation in the course of their continuing evolution (Gusella, J. F., *Ann. Rev. Biochem.* 55:831–854 (1986)). Since such mutations are not immediately transmitted throughout all of the members of a species, the evolutionary process creates polymorphic alleles that co-exist in the species populations. In some instances, such co-existence is in stable or quasi-stable equilibrium. In other instances, the mutation confers a survival or evolutionary advantage to the species, and accordingly, it may eventually (i.e. over evolutionary time) be incorporated into the DNA of every member of that species.

Several classes of polymorphisms have been identified. Variable nucleotide type polymorphisms ("VNTRs"), for example arise from spontaneous tandem duplications of di- or tri-nucleotide repeated motifs of nucleotides (Weber, J. L., U.S. Pat. No. 5,075,217; Armour, J.A.L. et al., *FEBS Lett.* 307:113–115 (1992); Jones, L. et al., *Eur. J. Haematol.* 39:144–147 (1987); Horn, G. T. et al., PCT Application WO91/14003; Jeffreys, A. J., European Patent Application 370,719; Jeffreys, A. J., U.S. Pat. No. 5,175,082); Jeffreys. A. J. et al., *Amer. J. Hum. Genet.* 39:11–24 (1986); Jeffreys. A. J. et al., *Nature* 316:76–79 (1985); Gray, I. C. et al., *Proc. R. Acad. Soc.* Lond. 243:241–253 (1991); Moore, S. S. et al., *Genomics* 10:654–660 (1991); Jeffreys, A. J. et al., *Anim. Genet.* 18:1–15 (1987); Hillel, J. et al., *Anim. Genet.* 20:145–155 (1989); Hillel, J. et al., *Genet.* 124:783–789 (1990)). If such a variation alters the lengths of the fragments that are generated by restriction endonuclease cleavage, the variations are referred to as restriction fragment length polymorphisms ("RFLPs"). RFLPs have been widely used in human and animal genetic analyses (Glassberg, J., UK patent application 2135774; Skolnick, M. H. et al., *Cytogen. Cell Genet.* 32:58–67 (1982); Botstein, D. et al., *Ann. J. Hum. Genet.* 32:314–331 (1980); Fischer, S. G et al. (PCT Application WO90/13668); Uhlen, M., PCT Application WO90/11369)).

Most polymorphisms arise from the replacement of only a single nucleotide from the initially present gene sequence. In rare cases, such a substitution can create or destroy a particular restriction site, and thus may comprise an RFLP polymorphism. In many cases, however, the substitution of a nucleotide in such single nucleotide polymorphisms cannot be determined by restriction fragment analysis. In some cases, such polymorphisms comprise mutations that are the determinative characteristic in a genetic disease. Indeed, such mutations may affect a single nucleotide in a protein-encoding gene in a manner sufficient to actually cause the disease (i.e., hemophilia, sickle-cell anemia, etc.). Despite the central importance of such polymorphisms in modern genetics, few methods have been developed that could permit the comparison of the alleles of two individuals at many such polymorphisms in parallel.

II. The Attributes of the Single Nucleotide Polymorphisms of the Present Invention and The Advantages of their Use in Genetic Analysis A "polymorphism" is a variation in the DNA sequence of some members of a species. A polymorphism is thus said to be "allelic," in that, due to the existence of the polymorphism, some members of a species may have the unmutated sequence (i.e. the original "allele") whereas other members may have a mutated sequence (i.e. the variant or mutant "allele"). In the simplest case, only one mutated sequence may exist, and the polymorphism is said to be diallelic. In the case of diallelic diploid organisms, three genotypes are possible. They can be homozygous for one allele, homozygous for the other allele or heterozygous. In the case of diallelic haploid organisms, they can have one allele or the other, thus only two genotypes are possible. Diallelic polymorphisms are the preferred polymorphisms of the present invention. The occurrence of alternative mutations can give rise to trialleleic, etc. polymorphisms. An allele may be referred to by the nucleotide(s) that comprise the mutation. The present invention is directed to a particular class of allelic polymorphisms, and to their use in genotyping a plant or animal. Such allelic polymorphisms are referred to herein as "single nucleotide polymorphisms," or "SNPs." "Single nucleotide polymorphisms" are defined by their characteristic attributes. A central attribute of such a polymorphism is that it contains a polymorphic site, "X," most preferably occupied by a single nucleotide, which is the site of the polymorphism's variation (Goelet, P. and Knapp, M., U.S. Pat. application Ser. No. 08/145,145, herein incorporated by reference).

SNPs have several salient advantages over RFLPs and VNTRs. First, SNPs are more stable than other classes of polymorphisms. Their spontaneous mutation rate is approximately $10^{-9}$ (Kornberg, A., *DNA Replication*, W. H. Freeman & Co., San Francisco, 1980), approximately 1,000 times less frequent than VNTRs. Significantly, VNTR-type polymorphisms are characterized by high mutation rates.

Second, SNPs occur at greater frequency, and with greater uniformity than RFLPs and VNTRs. The characterization of VNTRs and RFLPs is highly dependent upon the method used to detect the polymorphism. In contrast, because SNPs result from sequence variation, new polymorphisms can be identified by sequencing random genomic or cDNA molecules. VNTRs and RFLPs can also be considered a subset of SNPs because variation in the region of a VNTR or RFLP can result in a single-base change in the region. SNPs can also result from deletions, point mutations and insertions. Any single base alteration, whatever the cause, can be a SNP. The greater frequency of SNPs means that they can be more readily identified than the other classes of polymorphisms. The greater uniformity of their distribution permits the identification of SNPs "nearer" to a particular trait of interest. The combined effect of these two attributes makes SNPs extremely valuable. For example, if a particular trait (e.g. predisposition to cancer) reflects a mutation at a particular locus, then any polymorphism that is linked to the particular locus can be used to predict the probability that an individual will be exhibit that trait.

SNPs can be characterized using any of a variety of methods. Such methods include the direct or indirect sequencing of the site, the use of restriction enzymes where the respective alleles of the site create or destroy a restriction site, the use of allele-specific hybridization probes, the use of antibodies that are specific for the proteins encoded by the different alleles of the polymorphism, or by other biochemical interpretation. However, no assay yet exists that is both highly accurate and easy to perform.

III. Methods of Analyzing Polymorphic Sites

A. DNA Sequencing

The most obvious method of characterizing a polymorphism entails direct DNA sequencing of the genetic locus that flanks and includes the polymorphism. Such analysis can be accomplished using either the "dideoxy-mediated chain termination method," also known as the "Sanger Method" (Sanger, F., et al., *J. Molec. Biol.* 94:441 (1975)) or the "chemical degradation method," "also known as the "Maxam-Gilbert method" (Maxam, A. M., et al., *Proc. Natl. Acad. Sci. (.U.S.A.)* 74:560 (1977)). In combination with genomic sequence-specific amplification technologies, such as the polymerase chain reaction (Mullis, K. et al., *Cold Spring Harbor Symp. Quant. Biol.* 51:263–273 (1986); Erlich H. et al., European Patent Appln. 50,424; European Patent Appln. 84,796, European Patent Application 258,017, European Patent Appln. 237,362; Mullis, K., European Patent Appln. 201,184; Mullis K. et al., U.S. Pat. No. 4,683,202; Erlich, H., U.S. Pat. No. 4,582,788; and Saiki, R. et al., U.S. Pat. No. 4,683,194)), may be employed to facilitate the recovery of the desired polynucleotides, direct sequencing methods are technically demanding, relatively expensive, and have low throughput rates. As a result, there has been a demand for techniques that simplify repeated and parallel analysis of SNPs.

B. Exonuclease Resistance

Mundy, C. R. (U.S. Pat. No. 4,656,127) discusses alternative methods for determining the identity of the nucleotide present at a particular polymorphic site. Mundy's methods employ a specialized exonuclease-resistant nucleotide derivative. A primer complementary to the allelic sequence immediately 3'-to the polymorphic site is permitted to hybridize to a target molecule obtained from a particular animal or human. If the polymorphic site on the target molecule contains a nucleotide that is complementary to the particular exonucleotide-resistant nucleotide derivative present, then that derivative will be incorporated by a polymerase onto the end of the hybridized primer. Such incorporation renders the primer resistant to exonuclease, and thereby permits its detection. Since the identity of the exonucleotide-resistant derivative of the sample is known, a finding that the primer has become resistant to exonucleases reveals that the nucleotide present in the polymorphic site of the target molecule was complementary to that of the nucleotide derivative used in the reaction. The Mundy method has the advantage that it does not require the determination of large amounts of extraneous sequence data. It has the disadvantages of destroying the amplified target sequences, and unmodified primer and of being extremely sensitive to the rate of polymerase incorporation of the specific exonuclease-resistant nucleotide being used.

C. Microsequencing Methods

Recently, several primer-guided nucleotide incorporation procedures for assaying polymorphic sites in DNA have been described (Komher, J. S. et al., *Nucl. Acids. Res.* 17:7779–7784 (1989); Sokolov, B. P., *Nucl. Acids Res.* 18:3671 (1990); Syvänen, A.-C., et al., *Genomics* 8:684–692 (1990); Kuppuswamy, M. N. et al., *Proc. Natl. Acad. Sci. (U.S.A.)*88:1143–1147 (1991); Prezant, T. R. et al., *Hum. Mutat.* 1:159–164 (1992); Ugozzoli, L. et al., *GATA* 9:107–112 (1992); Nyrén, P. et al., *Anal. Biochem.* 208:171–175 (1993)). These methods differ from Genetic Bit™ Analysis ("GBA™" discussed extensively below) in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvänen, A.-C., et al., *Amer. J. Hum. Genet.* 52:46–59 (1993)). Such a range of locus-specific signals could be more complex to interpret, especially for heterozygotes, compared to the simple, ternary (2:0, 1:1, or 0:2) class of signals produced by the GBA™ method. In addition, for some loci, incorporation of an incorrect deoxynucleotide can occur even in the presence of the correct dideoxynucleotide (Komher, J. S. et al., *Nucl. Acids. Res.* 17:7779–7784 (1989)). Such deoxynucleotide misincorporation events may be due to the Km of the DNA polymerase for the mispaired deoxy- substrate being comparable, in some sequence contexts, to the relatively poor Km of even a correctly base paired dideoxy- substrate (Kornberg, A., et al., In: DNA Replication, Second Edition (1992), W. H. Freeman and Company, New York; Tabor, S. et al., *Proc. Natl. Acad. Sci, (U.S.A.)* 86:4076–4080 (1989)). This effect would contribute to the background noise in the polymorphic site interrogation.

D. Extension in Solution using ddNTPs

Cohen, D. et al. (French Patent 2,650,840; PCT Appln. No. WO91/02087) discuss a solution-based method for determining the identity of the nucleotide of a polymorphic site. As in the Mundy method of U.S. Pat. No. 4,656,127, a primer is employed that is complementary to allelic sequences immediately 3'-to a polymorphic site. The method determines the identity of the nucleotide of that site using labeled dideoxynucleotide derivatives, which, if complementary to the nucleotide of the polymorphic site will become incorporated onto the terminus of the primer.

The method of Cohen has the significant disadvantage of being a solution-based extension method that uses labeled dideoxynucleoside triphosphates. The target DNA template is usually prepared by a DNA amplification reaction, such as the PCR, that uses a high concentration of deoxynucleoside triphosphates, the natural substrates of DNA polymerases. These monomers will compete in the subsequent extension reaction with the dideoxynucleoside triphosphates. Therefore, following the PCR, an additional purification step is required to separate the DNA template from the unincorporated dNTPs. Because it is a solution-based method, the unincorporated dNTPs are difficult to remove and the method is not suited for high volume testing.

E. Solid-Phase Extension using ddNTPs

An alternative method, known as Genetic Bit Analysis™ or GBA™ is described by Goelet, P. et al. (PCT Appln. No. 92/15712). In a preferred embodiment, the method of Goelet, P. et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Appln. No. WO91/02087) the method of Goelet, P. et al. is preferably a heterogeneous phase assay, in which the primer or the target molecule is immobilized to a solid phase. It is thus easier to perform, and more accurate than the method discussed by Cohen.

F. Oligonucleotide Ligation Assay

Another solid phase method that uses different enzymology is the "Oligonucleotide Ligation Assay" ("OLA") (Landegren, U. et el., Science 241:1077–1080 (1988). The OLA protocol uses two oligonucleotides which are designed to be capable of hybridizing to abutting sequences of a single strand of a target. One of the oligonucleotides is biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. OLA is capable of detecting point mutations. Nickerson, D. A. et al. have described a nucleic acid detection assay that combines attributes of PCR and OLA (Nickerson, D. A. et al., Proc. Natl. Acad. Sci. (U.S.A.)87:8923–8927 (1990). In this method, PCR is used to achieve the exponential amplification of target DNA, which is then detected using OLA. Assays, such as the OLA, require that each candidate dNTP of a polymorphism be separately examined, using a separate set of oligonucleotides for each dNTP. The major drawback of OLA is that ligation is not a highly discriminating process and non-specific signals can be a significant problem.

IV. Conclusions

As will be appreciated, most of the above-described methods require a polymerase to incorporate a nucleotide derivative onto the 3'-terminus of a primer molecule. It would be desirable to develop a more selective process for discriminating single nucleotide polymorphisms. The present invention satisfies this need by providing a ligase/polymerase-mediated method of determining the identity of the nucleotide present at a polymorphic site. The addition of a ligase to the process means that two events are required to generate a signal, extension and ligation. This grants the present invention a higher specificity and lower "noise" than methods using either extension or ligation alone. Unlike the oligonucleotide ligation assay, in the present invention, the distinguishing step of extension is mediated by polymerase and polymerases are more specific in their activity than ligases. Unlike the polymerase-based assays, this method enhances the specificity of the polymerase step by combining it with a second hybridization and a ligation step for a signal to be attached to the solid phase.

SUMMARY OF THE INVENTION

The present invention is directed to a ligase/polymerase-mediated method for determining the identity of the nucleotide present in a polymorphic site of an organism (either a microorganism, plant, a non-human animal, or a human). The invention is further directed to methods of using such information in genetic analysis.

In detail, the invention provides a method for determining the identity of a nucleotide present at a preselected single nucleotide site in a target nucleic acid molecule, the method comprising the steps:

A) immobilizing a first oligonucleotide (either linker or primer) to a solid support; the first oligonucleotide having a nucleotide sequence complementary to that of the target molecule, and being capable of hybridizing to the target molecule at a first region of the target molecule such that one terminus of the hybridized first oligonucleotide is immediately adjacent to the preselected site;

B) incubating the immobilized first oligonucleotide in the presence of the target molecule, and in the further presence of a second oligonucleotide (either linker or primer, the order of addition of the oligonucleotides being immaterial; the second oligonucleotide having a sequence complementary to that of the target molecule, and being capable of hybridizing to the target molecule at a second region of the target molecule, wherein the first and second regions are separated from one another by the preselected site; the incubation being under conditions sufficient to permit the first and second oligonucleotides to hybridize to the target molecule to thereby form a hybridized product in which the oligonucleotides are separated from one another by a space of a single nucleotide, the space being opposite to the preselected site;

C) further incubating the hybridized product, in the presence of a polymerase, a ligase, and a nucleoside triphosphate mixture containing at least one deoxynucleoside triphosphate; the incubation being under conditions sufficient to permit the template-dependent, polymerase mediated, incorporation of the nucleoside triphosphate onto a 3'-terminus of either of the immobilized first or second hybridized oligonucleotides, and thereby fill the space between these hybridized oligonucleotides, and cause the oligonucleotides to abut; the incorporation being dependent upon whether the nucleoside triphosphate mixture contains a nucleoside triphosphate that is complementary to the nucleotide present at the preselected site;

D) permitting the ligase to ligate together any pair of abutting first and second hybridized oligonucleotides;

E) further incubating the immobilized first oligonucleotide under conditions sufficient to separate any non-covalently bonded target or second oligonucleotide therefrom; and F) determining the identity of the nucleotide of the preselected site by determining whether the second oligonucleotide or one of the nucleoside triphosphates has become immobilized to the solid support.

The invention further includes the embodiments of the above method wherein the first and second oligonucleotides and the target molecule are DNA molecules, RNA molecules, peptide nucleic acids and other modified DNA molecules.

The invention also encompasses the embodiments of the above methods wherein in step A, the 3'-terminus of the first oligonucleotide (the "linker") is immobilized to the solid support, and wherein in step C, the conditions permit the incorporation of the nucleoside triphosphate onto the 3'-terminus of the second hybridized oligonucleotide (the "primer") or wherein in step A, the 5'-terminus of the first oligonucleotide is immobilized to the solid support, and wherein in step C, the conditions permit the incorporation of the nucleoside triphosphate onto the 3'-terminus of the first hybridized oligonucleotide (primer). Following incorporation, the primer and linker oligonucleotides are ligated together and the identity of the polymorphic nucleotide is determined from the signal associated with the solid phase.

The invention additionally concerns the embodiment of the above methods wherein one of the nucleoside triphosphates is detectably labeled (as with a hapten, an enzyme label, a fluorescent label, a radioisotopic label, or a chemiluminescent label).

The invention particularly concerns the embodiments of the above methods wherein in step C, the nucleoside triphosphate mixture contains one or more detectably labeled nucleoside triphosphate(s), the other unlabeled nucleoside triphosphates being either deoxynucleoside triphosphates or dideoxynucleoside triphosphates, and wherein in step F, the identity of the nucleotide of the preselected site is determined by detecting the label of the immobilized labeled deoxy- or dideoxynucleoside triphosphate.

The invention also concerns the embodiment of the above methods wherein the second oligonucleotide is detectably labeled. Wherein in step C, the nucleoside triphosphate mixture contains only one nucleoside triphosphate, the nucleoside triphosphate being a deoxynucleoside triphosphate with or without the other three dideoxynucleotide triphosphates, and wherein in step F, the identity of the nucleotide of the preselected site is determined by detecting the label of the immobilized labeled second oligonucleotide.

In another embodiment, steps A–D may be performed in solution and the ligated oligonucleotides captured onto a solid phase for detection.

In yet another embodiment, steps A–D may be performed in solution and detection of the ligated oligonucleotides performed in solution.

The invention includes the use of the above-described methods to analyze a polymorphism of any diploid organism including an animal selected from the group consisting of a horse, a sheep, a bovine, a canine, a feline, a plant and a human, as well as haploid organisms including bacteria, fungi and viruses.

DESCRIPTION OF THE PREFERRED EMBODIMENTS

Figure 1:
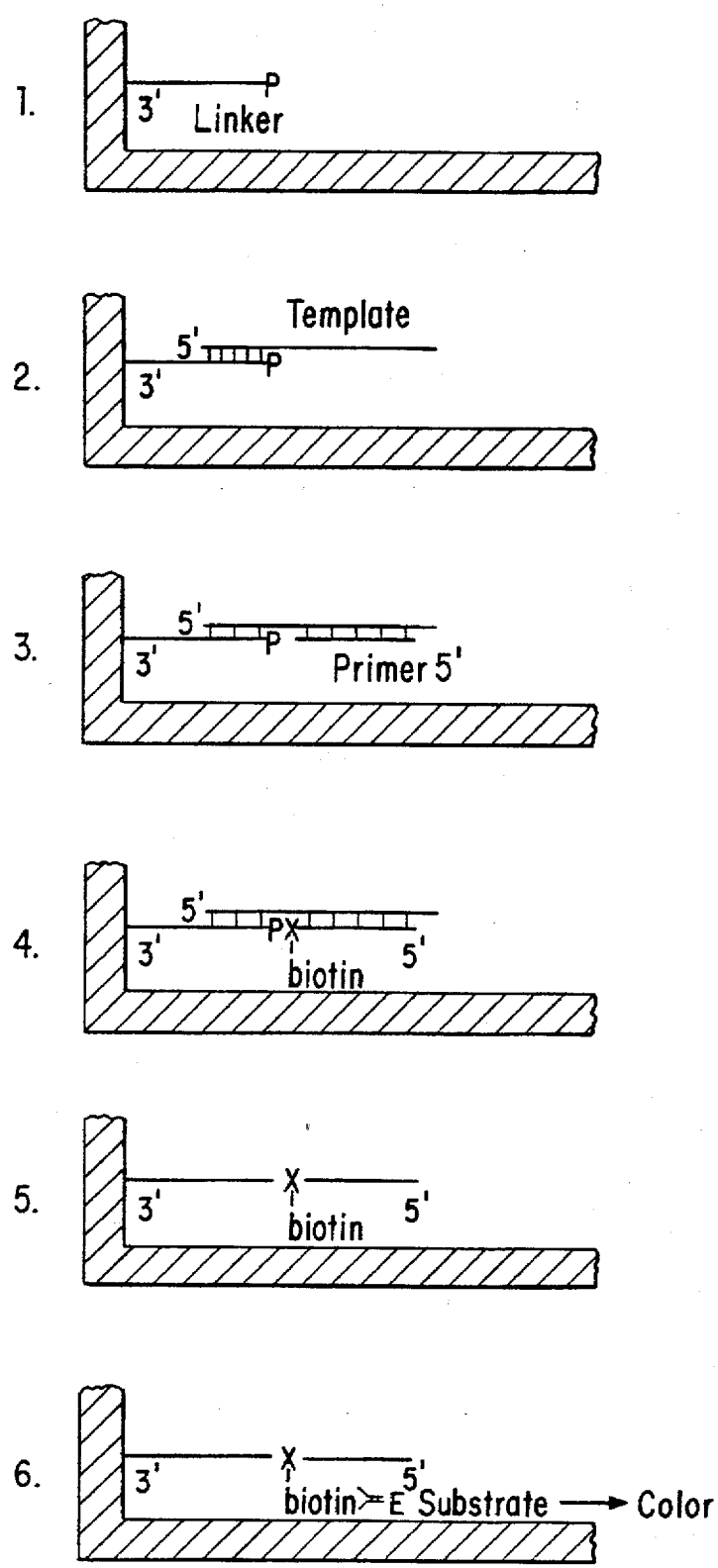
FIG. 1 is a diagram of a Ligase-Mediated GBA™ procedure using a labeled dNTP. In (1), a 5' phosphorylated linker oligonucelotide is bound to the surface of a microwell. In (2), template DNA is allowed to hybridize to the linker. In (3), a primer oligonucleotide hybridizes to the immobilized template. In (4), in the presence of DNA polymerase, ligase, a labeled dNTP and unlabeled dNTP(s), a labeled dNTP is incorporated and the linker and primer are ligated. In (5) The well is washed with alkali to remove all unligated DNA. In (6), The labeled base is detected using an enzyme conjugated antibody and substrate.

I. The Ligase/Polymerase-Mediated Assay of the Present Invention

A. Sample Preparation

Nucleic acid specimens may be obtained from an individual of the species that is to be analyzed using either "invasive" or "non-invasive" sampling means. A sampling means is said to be "invasive" if it involves the collection of nucleic acids from within the skin or organs of an animal (including, especially, a murine, a human, an ovine, an equine, a bovine, a porcine, a canine, or a feline animal). Examples of invasive methods include blood collection, semen collection, needle biopsy, pleural aspiration, etc. Examples of such methods are discussed by Kim, C. H. et al. (*J. Virol.* 66:3879–3882 (1992)); Biswas, B. et al. (*Annals NY Acad. Sci.* 590:582–583 (1990)); Biswas, B. et al. (*J. Clin. Microbiol.* 29:2228–2233 (1991)).

In contrast, a "non-invasive" sampling means is one in which the nucleic acid molecules are recovered from an internal or external surface of the animal. Examples of such "non-invasive" sampling means include "swabbing," collection of tears, saliva, urine, fecal material, sweat or perspiration, etc. As used herein, "swabbing" denotes contacting an applicator/collector ("swab") containing or comprising an adsorbent material to a surface in a manner sufficient to collect surface debris and/or dead or sloughed off cells or cellular debris. Such collection may be accomplished by swabbing nasal, oral, rectal, vaginal or aural orifices, by contacting the skin or tear ducts, by collecting hair follicles, etc.

B. Amplification of Target Sequences

The detection of polymorphic sites in a sample of DNA may be facilitated through the use of DNA amplification methods. Such methods specifically increase the concentration of sequences that span the polymorphic site, or include that site and sequences located either distal or proximal to it. Such amplified molecules can be readily detected by gel electrophoresis or other means.

The most preferred method of achieving such amplification employs PCR, using primer pairs that are capable of hybridizing to the proximal sequences that define a polymorphism in its double-stranded form.

C. Preparation of Single-Stranded DNA

The methods of the present invention do not require that the target nucleic acid contain only one of its natural two strands. Thus, the methods of the present invention may be practiced on either single-stranded DNA obtained by, for example, alkali treatment or native DNA. The presence of the unused (non-template) strand does not affect the reaction.

Where desired, any of a variety of methods can be used to eliminate one of the two natural stands of the target DNA molecule from the reaction. Single-stranded DNA molecules may be produced using the single-stranded DNA bacteriophage M13 (Messing, J. et al., *Meth. Enzymol.* 101:20 (1983); see also, Sambrook, J., et al. (In: *Molecular Cloning:A Laboratory. Manual*, Cold Spring Harbor Laboratory Press, Cold Spring Harbor, N.Y. (1989)).

Several alternative methods can be used to generate single-stranded DNA molecules. Gyllensten, U. et al., (*Proc. Natl. Acad. Sci.* (U.S.A.) 85:7652–7656 (1988) and Mihovilovic, M. et al., (*BioTechniques* 7(1):14 (1989)) describe a method, termed "asymmetric PCR," in which the standard "PCR" method is conducted using primers that are present in different molar concentrations. Higuchi, R. G. et al. (*Nucleic Acids Res.* 17:5865 (1985)) exemplifies an additional method for generating single-stranded amplification products. The method entails phosphorylating the 5'-terminus of one strand of a double-stranded amplification product, and then permitting a 5'→3' exonuclease (such as exonuclease) to preferentially degrade the phosphorylated strand.

Other methods have also exploited the nuclease resistant properties of phosphorothioate derivatives in order to generate single-stranded DNA molecules (Benkovic et al., U.S. Pat. No. 4,521,509; Jun. 4, 1985); Sayers, J. R. et al. (*Nucl. Acids Res.* 16:791–802 (1988); Eckstein, F. et al., *Biochemistry* 15:1685–1691 (1976); Ott, J. et al., *Biochemistry* 26:8237–8241 (1987)).

Most preferably, such single-stranded molecules will be produced using the methods described by Nikiforov, T. (U.S. patent application Ser. No. 08/005,061, herein incorporated by reference). In brief, these methods employ nuclease resistant nucleotide derivatives, and incorporate such derivatives, by chemical synthesis or enzymatic means, into primer molecules, or their extension products, in place of naturally occurring nucleotides.

Suitable nucleotide derivatives include derivatives in which one or two of the non-bridging oxygens of the phosphate moiety of a nucleotide has been replaced with a sulfur-containing group (especially a phosphorothioate), an alkyl group (especially a methyl or ethyl alkyl group), a nitrogen-containing group (especially an amine), and/or a selenium-containing group, for example. Phosphorothioate deoxyribonucleotide or ribonucleotide derivatives (e.g. a nucleoside 5'-O-1-thiotriphosphate) are the most preferred nucleotide derivatives. Any of a variety of chemical methods may be used to produce such phosphorothioate derivatives (see, for example, Zon, G. et al., *Anti-Canc. Drug Des.* 6:539–568 (1991); Kim, S. G. et al., *Biochem. Biophys. Res. Commun.* 179:1614–1619 (1991); Vu, H. et al., *Tetrahedron Lett.* 32:3005–3008 (1991); Taylor, J. W. et al., *Nucl. Acids Res.* 13:8749–8764 (1985); Eckstein, F. et al., *Biochemistry* 15:1685–1691 (1976); Ott, J. et al., *Biochemistry* 26:8237–8241 (1987); Ludwig, J. et al., *J. Org. Chem.* 54:631–635 (1989), all herein incorporated by reference).

Importantly, the selected nucleotide derivative must be suitable for in vitro primer-mediated extension and provide nuclease resistance to the region of the nucleic acid molecule in which it is incorporated. In the most preferred embodiment, it must confer resistance to exonucleases that attack double-stranded DNA from the 5'-end (5'→3' exonucleases). Examples of such exonucleases include bacteriophage T7 gene 6 exonuclease ("T7 exonuclease") and the bacteriophage lambda exonuclease ("exonuclease"). Both T7 exonuclease and exonuclease are inhibited to a significant degree by the presence of phosphorothioate bonds so as to allow the selective degradation of one of the strands. However, any double-strand specific, 5'→3' exonuclease can be used for this process, provided that its activity is affected by the presence of the bonds of the nuclease resistant nucleotide derivatives. The preferred enzyme when using phosphorothioate derivatives is the T7 gene 6 exonuclease, which shows maximal enzymatic activity in the same buffer used for many DNA dependent polymerase buffers including Taq polymerase. The 5'→3' exonuclease resistant properties of phosphorothioate derivative-containing DNA molecules are discussed, for example, in Kunkel, T. A. (In: *Nucleic Acids and Molecular Biology*, Vol. 2, 124–135 (Eckstein, F. et al., eds.), Springer-Verlag, Berlin, (1988)). The 3'→5'-exonuclease resistant properties of phosphorothioate nucleotide containing nucleic acid molecules are disclosed in Putney, S. D., et al. (*Proc. Natl. Acad. Sci.*(U.S.A.)78:7350–7354 (1981)) and Gupta, A. P., et al. (*Nucl. Acids. Res.*,12:5897–5911 (1984)).

D. Methods of Immobilization

Any of a variety of methods can be used to immobilize the linker or primer oligonucleotide to the solid support. One of the most widely used methods to achieve such an immobilization of oligonucleotide primers for subsequent use in hybridization-based assays consists of the non-covalent coating of these solid phases with streptavidin or avidin and the subsequent immobilization of biotinylated oligonucleotides (Holmstrom, K. et al., *Anal. Biochem.* 209:278–283 (1993)). Another recent method (Running. J. A. et al., *BioTechniques* 8:276–277 (1990); Newton, C. R, et al. *Nucl. Acids Res.* 21:1155–1162 (1993)) requires the precoating of the polystyrene or glass solid phases with poly-L-Lys or poly L-Lys, Phe, followed by the covalent attachment of either amino- or sulfhydryl-modified oligonucleotides using bifunctional crosslinking reagents. Both methods have the disadvantage of requiring the use of modified oligonucleotides as well as a pretreatment of the solid phase.

In another published method (Kawai, Set al., *Anal. Biochem.* 209:63–69 (1993)), short oligonucleotide probes were ligated together to form multimers and these were ligated into a phagemid vector. Following in vitro amplification and isolation of the single-stranded form of these phagemids, they were immobilized onto polystyrene plates and fixed by UV irradiation at 254 nm. The probes immobilized in this way were then used to capture and detect a biotinylated PCR product.

A method for the direct covalent attachment of short, 5'-phosphorylated primers to chemically modified polystyrene plates ("Covalink" plates, Nunc) has also been published (Rasmussen, S. R. et al., *Anal. Biochem*, 198:138–142 (1991)). The covalent bond between the modified oligonucleotide and the solid phase surface is introduced by condensation with a water-soluble carbodiimide. This method is claimed to assure a predominantly 5'-attachment of the oligonucleotides via their 5'-phosphates; however, it requires the use of specially prepared, expensive plates.

Most preferably, the immobilization of the oligonucleotides of the present invention is accomplished using a method that can be used directly, without the need for any pretreatment of commercially available polystyrene microwell plates (ELISA plates) or microscope glass slides (Nikiforov, T. and Knapp, M., U.S. patent application Ser. No. 08/162,397, herein incorporated by reference). Since 96 well polystyrene plates are widely used in ELISA tests, there has been significant interest in the development of methods for the immobilization of short oligonucleotide primers to the wells of these plates for subsequent hybridization assays. Also of interest is a method for the immobilization to microscope glass slides, since the latter are used in the so-called Slide Immunoenzymatic Assay (SIA) (de Macario, E. C. et al.. *BioTechniques* 3:138–145 (1985)).

The solid support can be glass, plastic, paper, etc. The support can be fashioned as a bead, dipstick, test tube, or a variety of other shapes. In a preferred embodiment, the support will be a microtiter dish, having a multiplicity of wells. The conventional 96-well microtiter dishes used in diagnostic laboratories and in tissue culture are a preferred support. The use of such a support allows the simultaneous determination of a large number of samples and controls, and thus facilitates the analysis. Automated delivery systems can be used to provide reagents to such microtiter dishes. Similarly, spectrophotometric methods can be used to analyze the polymorphic sites, and such analysis can be conducted using automated spectrophotometers.

In accordance with the present invention, any of a number of commercially available polystyrene plates can be used directly for the immobilization, provided that they have a hydrophilic surface. Examples of suitable plates include the Immulon 4 plates (Dynatech) and the Maxisorp plates (Nunc).

The immobilization of the oligonucleotides to the plates is achieved simply by incubation in the presence of a suitable salt (Nikiforov, T. and Knapp, M. PCT Appln. No. 08/162, 397, herein incorporated by reference). No immobilization takes place in the absence of a salt, i.e., when the oligonucleotide is present in a water solution. Examples for suitable salts are: 50–250 mM NaCl; 30–100 mM 1-ethyl-3-(3'-dimethylaminopropyl) carbodiimide hydrochloride (EDC), pH 6.8; 50–150 mM octyldimethylamine hydrochloride, pH 7.0; 50–250 mM tetramethylammonium chloride. The immobilization is achieved by incubation, preferably at room temperature for 3 to 24 hours. After such incubation, the plates are washed, preferably with a solution of 10 mM Tris HCl, pH 7.5, containing 150 mM NaCl and 0.05% vol. Tween 20 (TNTw). The latter ingredient serves the important role of blocking all free oligonucleotide binding sites still present on the polystyrene surface, so that no non-specific binding of oligonucleotides can take place during the subsequent hybridization steps. Using radioactively labeled oligonucleotides, the amount of immobilized oligonucleotides per well was determined to be at least 500 fmoles. The oligonucleotides are immobilized to the surface of the plate with sufficient stability and can only be removed by prolonged incubations with 0.5M NaOH solutions at elevated temperatures. No oligonucleotide is removed by washing the plate with water, TNTw (Tween 20), PBS, 1.5M NaCl, or other similar solutions.

This attachment method is extremely simple, works with any oligonucleotide and maintains the ability of the oligonucleotide to hybridize to its complementary sequence. In addition to microtiter plates, oligonucleotides may be immobilized onto miniature formats such as microscope slides and silicon chips. The oligonucleotides may also be applied to these formats in specific patterns using technologies such as ink-jet printing or photolithography. Detection of the patterns in these miniature formats can be accomplished by optical techniques using fluorescently-labeled nucleotides or oligonucleotides and instruments such as fluorescent microscopes.

E. Reaction Components and Conditions

Figure 2:
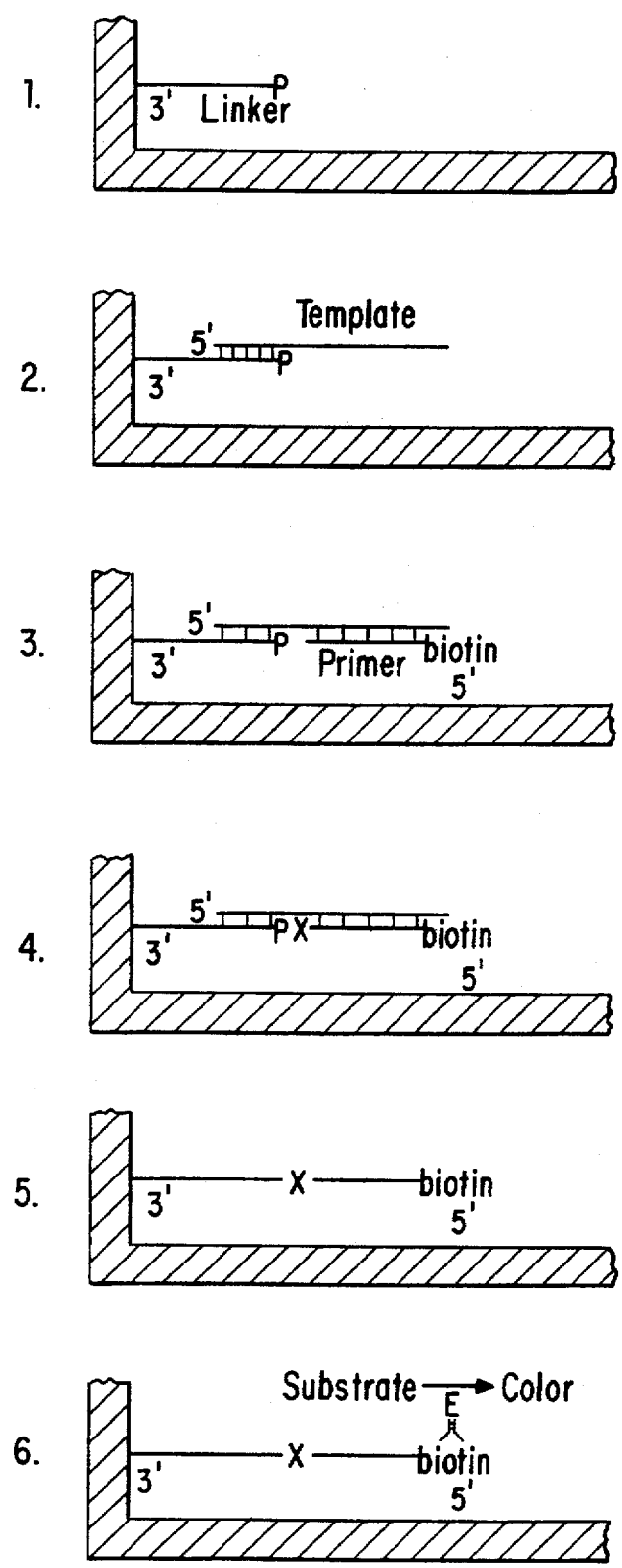
FIG. 2 is a diagram of a Ligase-Mediated GBA™ procedure using a labeled primer. In (1), a 5' phosphorylated linker oligonucelotide is bound to the surface of a microwell by its 3' end. In (2), template DNA is allowed to hybridize to the linker. In (3), a biotinylated primer oligonucleotide is allowed to hybridize to the immobilized linker. In (4), in the presence of DNA polymerase, ligase, a labeled dNTP and three unlabeled ddNTPs, the dNTP is incorporated and the linker and primer are ligated. In (5) the well is washed with alkali to remove all unligated DNA. In (6), the labeled base is detected using an enzyme conjugated antibody and substrate.
Figure 3:
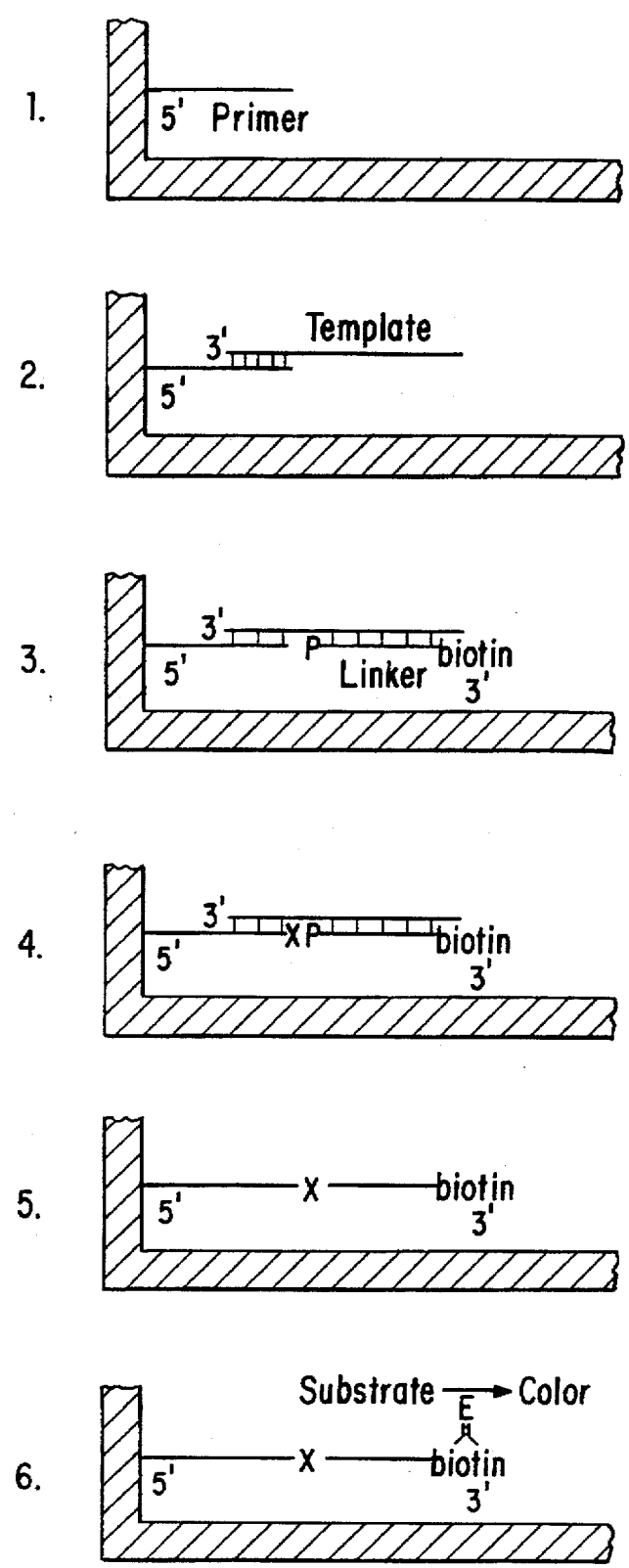
FIG. 3 is a diagram of a Ligase-Mediated GBA™ procedure using a labeled linker. In (1), a primer oligonucelotide is bound to the surface of a microwell by its 5' end. In (2), template DNA is allowed to hybridize to the linker. In (3), a 5' phosphorylated 3' biotinylated linker oligonucleotide hybridizes to the immobilized template. In (4), in the presence of DNA polymerase, ligase, a labeled dNTP and three ddNTPs, the dNTP is incorporated and the linker and primer are ligated. In (5) the well is washed with alkali to remove all unligated DNA. In (6), the labeled base is detected using an enzyme conjugated antibody and substrate.
Figure 4:
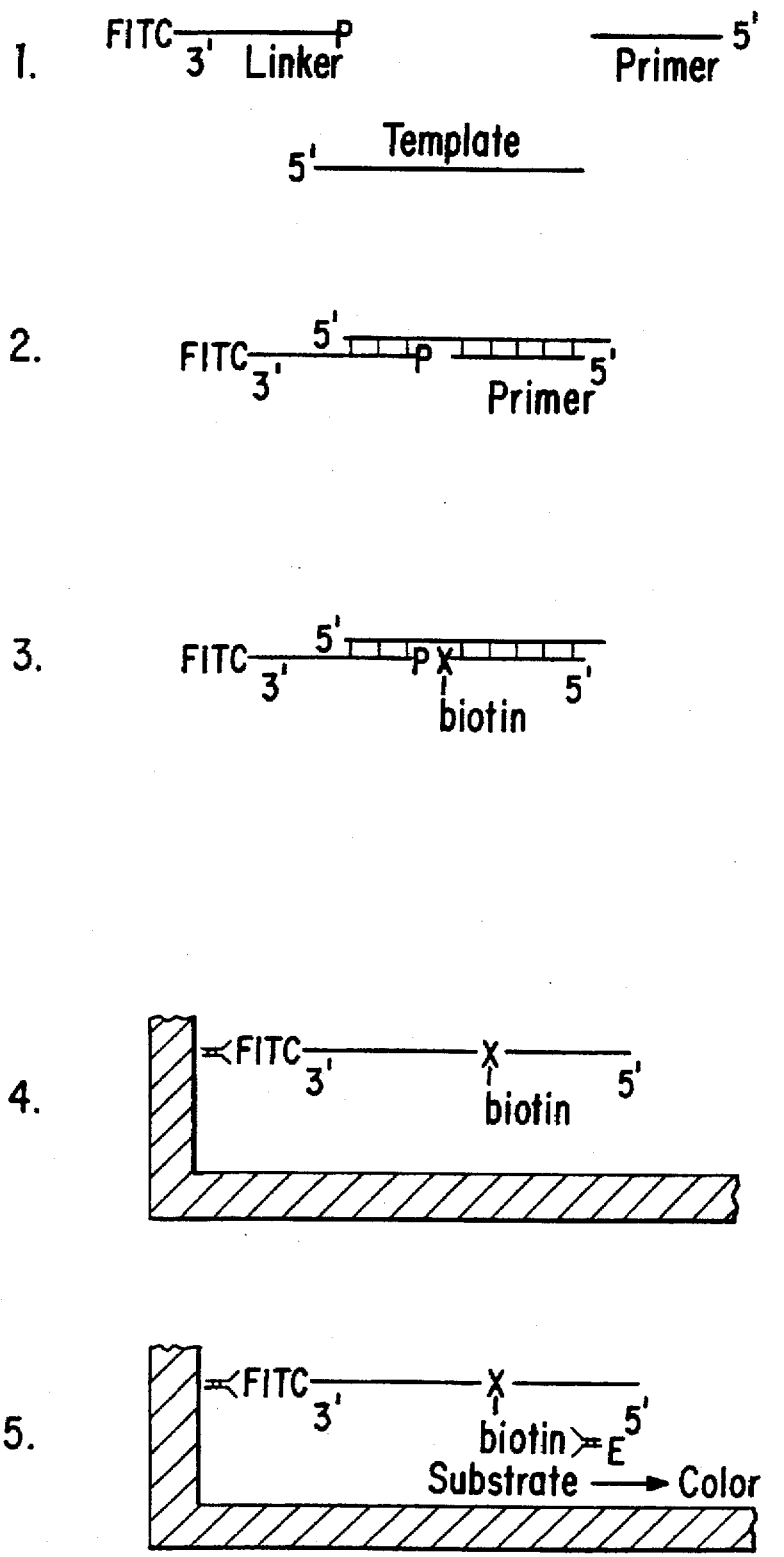
FIG. 4 is a diagram of a Ligase-Mediated GBA™ procedure in solution. In (1), a 5' phosphorylated, 3' fluoresceinated linker oligonucelotide is incubated with template DNA and a primer oligonucleotide. In (2), the three DNA molecules are allowed to hybridize in solution. In (3), in the presence of DNA polymerase, ligase, a labeled dNTP and unlabelled dNTP(s), a labeled dNTP is incorporated and the linker and primer are ligated. In (4) the ligated oligonucleotides are captured onto a solid phase and the well is washed to remove unligated DNA. In (5), the labeled base is detected using an enzyme conjugated antibody and substrate.

In its most preferred embodiment, the present invention comprises a heterogeneous phase assay in which one oligonucleotide is immobilized to a solid support. Three preferred variations or formats may be employed which perform equally well. These are: a) use of a labeled dNTP with an unlabeled linker oligonucleotide and an unlabeled primer oligonucleotide (FIG. 1); b) use of a labeled primer oligonucleotide with an unlabeled linker oligonucleotide and no labeled dNTPs (FIG. 2); c) use of a labeled linker oligonucleotide with an unlabeled primer oligonucleotide and no labeled dNTPs (FIG. 3). The order of the oligonucleotides can be varied, but the direction of extension is always 3' to 5' as determined by the polymerase. Hybridization, extension and ligation may also be performed in solution and the ligated oligonucleotides captured onto a solid phase for detection (FIG. 4).

The immobilized oligonucleotide is of a length sufficient to permit the molecule to stably and specifically hybridize to a complementary molecule. As used herein, "stable" hybridization refers to a hybridization that has a $T_m$ greater than the temperature under which the interrogation assay is to be run (generally 20°–40° C.). The term "specific" hybridization denotes that the length and/or sequence complexity of the oligonucleotides involved in the hybridization are sufficient to preclude non-desired spurious hybridization (as might occur, for example, between sequences that are only partially complementary). The hybridization is usually carried out for 15 to 30 minutes at room temperature in a solution containing 1.5M NaCl and 10 mM EDTA. Other hybridization conditions can alternatively be used. The sequence of the immobilized oligonucleotide is selected such that it will hybridize to the invariant sequence that flanks the polymorphic site of the polymorphism that is to be interrogated.

In the preferred embodiment, the immobilized oligonucleotide is the linker, tethered to the solid support by its 3'-end. The linker oligonucleotide in this embodiment acts to link (after extension and ligation) the incorporated nucleotide and primer oligonucleotide to the solid phase.

The reaction is then conducted in the presence of both the target sequence (that contains the polymorphism), and a second oligonucleotide, whose sequence is selected such that when the immobilized oligonucleotide and the second oligonucleotide are both hybridized to the same target molecule, the 3'-terminus of the primer oligo, and the 5'-terminus of the linker oligonucleotide will be separated by a "space" of a single base, precisely positioned opposite the variable nucleotide site, X, of the polymorphism.

One labeled 2'-deoxynucleoside 5'-triphosphate of DNA is added to the reaction along with three unlabeled dNTPs. This allows all primer molecules in the reaction to be extended and ligated. The unlabeled nucleoside triphosphates may also be dideoxynucleoside triphosphates, such that the incorporation of more than a single nucleotide onto the primer terminus will be prevented and strand displacement will also potentially be prevented. This differs from GBA™ because GBA™ incorporates a ddNTP, rather than a dNTP, onto the primer during extension.

A polymerase is present in the reaction, and the reaction conditions are maintained such that the 3'-terminus of the primer oligonucleotide is extended by a single nucleotide (i.e. the nucleotide opposite the variable site of the polymorphism).

The desired primer extension will occur only if the second oligonucleotide has correctly hybridized to the target molecule. The extension of the hybridized primer oligonucleotide "fills in" the space, and thereby permits the linker and primer oligonucleotides to be ligated to one another.

The presence of ligase in the reaction joins the abutting oligonucleotides. A variety of ligases can be used including T4 DNA ligase, E. coli DNA ligase, thermostable DNA ligase and RNA ligase. After ligation, the reaction vessel is washed or otherwise treated so as to effect the removal of any nucleic acid not bound to the solid support. As will be recognized, a ligatable substrate is formed only if the target molecule has indeed hybridized to both the first and second oligonucleotide and if the second oligonucleotide has been appropriately extended by the polymerase. Such ligation results in the immobilization of the previously non-tethered primer oligonucleotide. Thus, the primer oligonucleotide is extended with a labeled nucleotide, and immobilization of the label will result.

Significantly, such immobilization is dependent upon the incorporation of the complementary nucleoside opposite the polymorphic site, X. Thus, the immobilization of label reveals that the nucleoside triphosphate added to the reaction was complementary to the variable nucleoside triphosphate of the polymorphic site. In the preferred embodiment, if only the linker oligonucleotide has hybridized to a particular target molecule, then no ligatable substrate is formed, and the label (of the nucleotide) is not immobilized. Similarly, if, in the preferred embodiment, only the primer oligonucleotide has hybridized to the target molecule, then immobilization will not occur, and the labeled molecule will be lost upon washing.

In a second embodiment, the immobilized oligonucleotide is the linker, tethered to the solid support by its 3'-end. The reaction is conducted as described above, but the label is on the 5'-end of the primer oligonucleotide (FIG. 2).

In a third embodiment, the immobilized oligonucleotide is the primer, tethered to the solid support by its 5'-end. The reaction is conducted as described above, but the label is on the 3'-end of the linker oligonucleotide (FIG. 3).

In a fourth embodiment, hybridization, extension and ligation may be performed in solution and the ligated oligonucleotides captured onto a solid phase for detection (FIG. 4).

In a fifth embodiment, hybridization, extension and ligation may be performed in solution and the ligated oligonucleotides detected in solution.

Any of the conventionally used radioisotopic, enzymatic, fluorescent or chemiluminescent labels may be used in accordance with the methods of the present invention in lieu of such labels, haptenic labels, such as biotin or other labels such as ligands, antigens, etc. may be used. Suitable labels are disclosed, for example, by Kourilsky et al. (U.S. Pat. No. 4,581,333), Albarella et al., (EP 144914), Sheldon III et al. (U.S. Pat. No. 4,582,789), Albarella et al. (U.S. Pat. No. 4,563,417), and Miyoshi et al. (EP 119448)

In a preferred embodiment, the reaction will contain a single labeled nucleoside triphosphate, and three unlabeled nucleoside triphosphates. If the labeled nucleoside is complementary to the nucleotide of the preselected site, it will, in accordance with above methods, lead to the immobilization of the second, primer oligonucleotide. Thus, the identity of the nucleotide of the preselected site is determined by detecting the retention of label on the solid support after washing.

The ligase/polymerase mediated polymorphism interrogation method of the present invention is an improvement over the above-discussed GBA™ method. About 15–20% of the GBA™ primers direct the incorporation of certain ddNTPs even in the absence of a template (template-independent noise). This template independent noise results from the presence of self-complementary sequences within the primer molecules that can be extended by the polymerase. This template-independent extension is reduced in the presence of a template, and can be minimized in either of two ways. First, the base that is acting as a template and is responsible for the incorporation of a specific ddNTP can be replaced by a different base, such that the template-independent extension will be directed by a base that will not interfere with the typing of the polymorphisms. This is possible with diallelic loci. Second, the particular base within the primer can be replaced by an abasic 1,3-propanediol linker, which will prevent the polymerase from extending by any base. Thus, although GBA™ produces accurate results, a procedure that would be less subject to template-independent incorporation would be highly desirable.

GBA™ may also suffer from template-dependent noise, which is incorporation of a nucleotide not complementary to the polymorphic site nucleotide, onto the GBA™ primer. Template-dependent noise can be caused by several factors. First, the GBA™ primer can hybridize nonspecifically, thereby directing the incorporation of a labeled ddNTP at an irrelevant position. Second, the GBA™ primer may hybridize properly, but its 3'-end can slide along the template during the polymerase extension step by a few bases and again direct the incorporation of an irrelevant base. Third, even if the above causes are eliminated, it is possible that the polymerase has a relatively high rate of misincorporation. This rate is expected to be higher with the unnatural labeled ddNTPs used in the extension step than with the natural dNTP substrates.

II. The Use of Ligase/Polymerase-Mediated Interrogation of SNPs in Genetic Analysis A. General Considerations for Using Single Nucleotide Polymorphisms in Genetic Analysis The utility of the polymorphic sites of the present invention stems from the ability to use such sites to predict the statistical probability that two individuals will have the same alleles for any given polymorphism.

Such statistical analysis can be used for any of a variety of purposes. Where a particular animal has been previously tested, such testing can be used as a "fingerprint" with which to determine if a certain animal is, or is not, that particular animal. Where a putative parent or both parents of an individual have been tested, the methods of the present invention may be used to determine the likelihood that a particular animal is or is not the progeny of such parent or parents. Thus, the detection and analysis of SNPs can be used to exclude paternity of a male for a particular individual (such as a stallion's paternity of a particular foal), or to assess the probability that a particular individual is the progeny of a selected female (such as a particular foal and a selected mare).

The polymorphisms detected in a set of individuals of the same species (such as humans, horses, etc.), or of closely related species, can be analyzed to determine whether the presence or absence of a particular polymorphism correlates with a particular trait.

To perform such polymorphic analysis, the presence or absence of a set of polymorphisms (i.e. a "polymorphic array") is determined for a set of the individuals, some of which exhibit a particular trait, and some of which exhibit a mutually exclusive characteristic (for example, with respect to horses, brittle bones vs. non-brittle bones; maturity onset blindness vs. no blindness; predisposition to asthma or cardiovascular disease vs. no such predisposition). The alleles of each polymorphism of the set are then reviewed to determine whether the presence or absence of a particular allele is associated with the particular trait of interest. Any such correlation defines a genetic map of the individual's species. Alleles that do not segregate randomly with respect to a trait can be used to predict the probability that a particular animal will express that characteristic. For example, if a particular polymorphic allele is present in only 20% of the members of a species that exhibit a cardiovascular condition, then a particular member of that species containing that allele would have a 20% probability of exhibiting such a cardiovascular condition. As indicated, the predictive power of the analysis is increased by the extent of linkage between a particular polymorphic allele and a particular characteristic. Similarly, the predictive power of the analysis can be increased by simultaneously analyzing the alleles of multiple polymorphic loci and a particular trait. In the above example, if a second polymorphic allele was found to also be present in 20% of members exhibiting the cardiovascular condition, however, all of the evaluated members that exhibited such a cardiovascular condition had a particular combination of alleles for these first and second polymorphisms, then a particular member containing both such alleles would have a very high probability of exhibiting the cardiovascular condition.

The detection of multiple polymorphic sites permits one to define the frequency with which such sites independently segregate in a population. If, for example, two polymorphic sites segregate randomly, then they are either on separate chromosomes, or are distant to one another on the same chromosome. Conversely, two polymorphic sites that are co-inherited at significant frequency are linked to one another on the same chromosome. An analysis of the frequency of segregation thus permits the establishment of a genetic map of markers.

The present invention facilitates the construction of a genetic map of a target species. Thus, a particular array of polymorphisms can be correlated with a particular trait, in order to predict the predisposition of a particular animal (or plant) to such genetic disease, condition, or trait. As used herein, the term "trait" is intended to encompass "genetic disease," "condition," or "characteristics." The term, "genetic disease" denotes a pathological state caused by a mutation, regardless of whether that state can be detected or is asymptomatic. A "condition" denotes a predisposition to a characteristic (such as asthma, weak bones, blindness, ulcers, cancers, heart or cardiovascular illnesses, skeletomuscular defects, etc.). A "characteristic" is an attribute that imparts economic value to a plant or animal. Examples of characteristics include longevity, speed, endurance, rate of aging, fertility, etc.

The resolution of a genetic map is proportional to the number of markers that it contains. Since the methods of the present invention can be used to isolate a large number of polymorphic sites, they can be used to create a map having any desired degree of resolution.

The sequencing of the polymorphic sites greatly increases their utility in gene mapping. Such sequences can be used to design oligonucleotide primers and probes that can be employed to "walk" down the chromosome and thereby identify new marker sites (Bender, W. et al., *J. Supra. Molec. Struc.* 10(suppl.):32 (1979); Chinault, A. C. et al., *Gene* 5:111–126 (1979); Clarke, L. et al., *Nature* 287:504–509 (1980)).

The resolution of the map can be further increased by combining polymorphic analyses with data on the phenotype of other attributes of the plant or animal whose genome is being mapped. Thus, if a particular polymorphism segregates with brown hair color, then that polymorphism maps to a locus near the gene or genes that are responsible for hair color. Similarly, biochemical data can be used to increase the resolution of the genetic map. In this embodiment, a biochemical determination (such as a serotype, isoform, etc.) is studied in order to determine whether it co-segregates with any polymorphic site. Such maps can be used to identify new gene sequences, to identify the causal mutations of disease, for example.

Indeed, the identification of the SNPs of the present invention permits one to use complimentary oligonucleotides as primers in PCR or other reactions to isolate and sequence novel gene sequences located on either side of the SNP. The invention includes such novel gene sequences. The genomic sequences that can be clonally isolated through the use of such primers can be transcribed into RNA, and expressed as protein. The present invention also includes such protein, as well as antibodies and other binding molecules capable of binding to such protein.

In addition to identifying the SNPs of macroscopic plants and animals, the present method should be useful for genotyping microorganisms. One example would be the typing of Human Immunodeficiency Virus Type 1 (HIV-1) and HIV-2. The rapid typing of HIV from infected patients may play an important role in the development and monitoring of potential vaccines, since certain vaccines may only be effective against specific HIV strains. HIV typing may also be important in the monitoring of therapeutic trials and to qualify patients for potential treatment. Another example of a virus that may require rapid typing is Hepatitis C Virus (HCV), in order to track its source, predict the course of HCV disease and to determine appropriate treatment. An example of bacterial genotyping is the typing of *Mycobacterium tuberculosis* strains for epidemiological studies, to distinguish it from *Mycobacterium bovis* and to rapidly detect multi-drug resistant strains.

The invention is illustrated below with respect to one of its embodiments—horses and equine genetics. Because the fundamental tenets of genetics apply irrespective of species, such illustration is equally applicable to any other species, including humans. Those of ordinary skill would therefore need only to directly employ the methods of the above invention to analyze SNPs in any other species, and to thereby conduct the genetic analysis of the present invention.

Having now generally described the invention, the same will be more readily understood through reference to the following examples of the isolation and analysis of equine polymorphisms which are provided by way of illustration, and are not intended to be limiting of the present invention.

EXAMPLE 1

Analysis of an Equine Polymorphism using Labeled dNTPs and Unlabeled ddNTPs

In order to interrogate a single-nucleotide equine polymorphism, the following oligonucleotides were used (p denotes phosphate group):

1654 SEQ ID NO:1 5'p-GTGGAGATCACAGACTGAAATATTG-p

1112 SEQ ID NO:2 AGTATAATAATCACAGTATGT-TAGC

1214 SEQ ID NO:3 ACCTTCAAAACTCAACT-CAGCTCTT

1215 SEQ ID NO:4 TTTACCAATGAGAAGGA-CATCTAAG

Oligonucleotides #1654 and #1112 were used in the solid phase extension/ligation assay; oligonucleotides #1214 and #1215 were the PCR primers used to amplify the desired fragment of the equine genomic DNA. The PCR primer #1214 was modified at its 5'-end by the introduction of four phosphorothioate bonds. These served to protect one of the strands of the double-stranded PCR product from hydrolysis by T7 gene 6 exonuclease. The phosphorothioate bonds are located between the underlined residues of the sequence.

PCR Amplification

Horse genomic DNA was the source of DNA in the PCR amplification reaction. The reaction was carried out in total volume of 50 µl. The final concentration of the PCR primers was 0.5 µM. Following an initial two minute denaturation step at 95° C., thirty-five cycles were carried out, each consisting of denaturation (1 min at 95° C.), annealing (2 min at 60° C.) and extension (3 min at 72° C.). Taq DNA polymerase was obtained from Perkin-Elmer and used at a concentration of 0.025 u/µl. The final composition of the PCR buffer was: 1.5 mM $MgCl_2$, 50 mM KCl, 10 mM Tris-HCl, pH 8.3 and 200 µg/ml BSA.

Preparation of Single-Stranded PCR Products

In order to protect one of the strands of the double-stranded PCR product from exonuclease hydrolysis, four phosphorothioate bonds were introduced during synthesis at the 5'-end of one of the PCR primers (#1214). For generation of a single-stranded PCR product, following PCR amplification, T7 gene 6 exonuclease was added to a final concentration of 2 units/µl of PCR reaction. Incubation was for one hour at room temperature. The T7 gene 6 exonuclease was purchased from USB and diluted in a buffer recommended by the manufacturer.

Hybridization of Single-Stranded PCR Fragments to Oligonucleotides Immobilized in Microtiter Plates After the exonuclease treatment, an equal volume of 3M NaCl, 20 mM EDTA was added to the reaction mixture and 20 µl aliquots of the resulting solution transferred to individual wells containing the immobilized oligonucleotide #1654. To the hybridization solution was added 1.5 pmole of the oligonucleotide primer #1112. Hybridization was carried out for 30 minutes at room temperature and was followed by washing with TNTw.

Extension/Ligation Reaction

The extension/ligation mixture had the following composition: 20 mM Tris-HCl, pH 7.5; 10 mM $MgCl_2$; 25 mM NaCl; 1 mM ATP; 0.65 units/well Sequenase and 0.4 units/well of T4 DNA ligase. In addition, some of the wells contained 30 µM biotin-14-dCTP (obtained from GIBCO-BRL) and 30 µM each of the other ddNTPs. Other wells contained 30 µM biotin-dCTP (GIBCO-BRL) and 30 µM each of the other ddNTPs. The extension/ligation reaction was allowed to proceed for 15 minutes at room temperature, then the wells were washed with 0.1N NaOH to remove all molecules not covalently bound to the immobilized oligonucleotide. The wells were subsequently incubated with a 1:1200 dilution of anti-biotin horseradish peroxidase conjugate (Vector Laboratories) in TNTw containing 1% BSA for 30 minutes at room temperature. The plate was washed six times with TNTw, then a solution of 0.1M citrate buffer, pH 4.5 containing 1 mg/ml o-phenylenediamine (OPD) and 0.012% $H_2O_2$ was added. The plate was immediately read in a plate reader and the color development was followed at 450 nm for 2 minutes. The results (expressed as mOD/min) obtained for three different horses are summarized in Table 1.

TABLE 1

| Horse No. | A Signal | C Signal | T Signal |
|---|---|---|---|
| 1534 | 0.4 | 382.1 | 1.7 |
| 866 | 0.3 | 302.0 | 96.8 |
| 527 | 0.2 | 0.9 | 161.9 |
| No DNA | 0.3 | 0.5 | 0.3 |

The results in Table 1 show that for this polymorphic locus, horse #1534 is a C homozygote, horse #866 is a CT heterozygote and horse #527 is a T homozygote.

EXAMPLE 2

Ligase/Polymerase Mediated Genetic Bit™ Analysis of a Single-Nucleotide Polymorphism using Unlabeled dNTPs, ddNTPs and a Labeled Oligonucleotide Linker Molecule Oligonucleotides used (FI denotes a fluorescein residue):
1401   SEQ   ID   NO:5
5'-TTCTCCCAGTGGCACAGTAAAATT-FI-G
713-1   SEQ   ID   NO:6
5'-GCTTCTACATTCATTTTCTTGTTCT
1376   SEQ   ID   NO:7
5'-AATTTTACTGTGCCACTGGGAGAACA GAA-CAAGAAAATGAATGTAGAAGC In this experiment, oligonucleotide #1376 was used as a synthetic template which should hybridize to both the oligonucleotide primer #713-1 and to the labeled linker molecule #1401. The underlined base in the sequence of #1376 serves as a model single-nucleotide polymorphism.

The oligonucleotide primer #713-1 was immobilized in the wells of a 96 well polystyrene plate (Immulon 4, Dynatech). It was hybridized to the synthetic template molecule #1376, in the presence of the labeled oligonucleotide #1401. The following amounts of #1376 were used: 250 and 500 fmole per well. Oligonucleotide #1401 was used in excess (1.5 pmole per well). Hybridization was carried out as described above in Example 1. The plate was washed and the extension/ligation reaction was carried out as described above, but in the presence of unlabeled nucleotides only, all at a concentration of 30 µM. The following four nucleotide mixtures were used: dATP plus ddGTP, ddCTP and ddTTP; dCTP plus ddATP, ddGTP and ddTTP; dGTP plus ddATP, ddCTP and ddTTP; dTTP plus ddATP, ddGTP and ddCTP. Following the extension/ligation reaction, the plate was washed with 0.1N NaOH in order to remove all molecules not covalently bound to the immobilized oligonucleotide. The presence of fluorescein in the wells was then detected using an anti-fluorescein horseradish peroxidase conjugate (DuPont) at a dilution of 1:500 in TNTw containing 1% BSA for 30 minutes at room temperature. Enzyme detection was performed as described in Example 1. The results are summarized in Table 2.

TABLE 2

| Template | A Signal | C Signal | G Signal | T Signal |
|---|---|---|---|---|
| 250 fmole | 25.0 | 26.5 | 185.3 | 23.5 |
| 500 fmole | 50.0 | 43.5 | 380.6 | 42.6 |

As a control, a similar reaction was carried out, but the polymerase was omitted from the extension mixture. These results are in Table 3.

TABLE 3

| Template | A Signal | C Signal | G Signal | T Signal |
|---|---|---|---|---|
| 250 fmole | 33.5 | 30.8 | 35.8 | 32.5 |
| 500 fmole | 55.5 | 60.6 | 60.3 | 55.1 |

These results clearly revealed the nature of the polymorphic base to be a C.

EXAMPLE 3

Analysis of an Equine Polymorphism using a Labeled dNTP and Unlabeled dNTPs.

In order to interrogate a particular equine polymorphism, two oligonucleotides were synthesized. The molecules had the sequences:

1357    SEQ ID NO:8
5'-PCTCCCAGTGGCACAGTAAAATTGGTP ("linker")

713    SEQ ID NO:9
5'-TTCTACATTCATTTTCTTGTTCTGT ("primer")

Oligonucleotide #1357 was phosphorylated on both its 3' and 5'-termini; oligonucleotide #713 lacked terminal phosphates.

Oligonucleotide #1357 was attached to the wells of a 96 well polystyrene plate using N-ethyl-N'-(3-dimethylamino)propylcarbodiimide hydrochloride (EDC). After washing to remove unbound material, approximately 250 fmol of an amplified 55 bp equine genomic sequence was added. The equine sequence was produced via PCR from equine genomic DNA. The amplified product contained the following sequence:

SEQ ID NO:10 5'-ACCAATTTTACTGTGCCACTGGGA GAACAGAACAAGAAAATGAATGT TAGAAGCAT

The hybridization was carried out for 30 minutes at room temperature in 1.5M NaCl, 10 mM EDTA. Also present during the hybridization step was 1 pmol of the second oligonucleotide (#713). Both oligonucleotides (#713 and #1357) hybridize to the PCR product, leaving between the 3'-end of #713 and the 5'-end of #1357 a space of exactly 1 base, located opposite residue A26 in SEQ ID NO:10.

Following the hybridization step, the plate was washed and the wells containing the hybridization complex incubated with the extension-ligation mixture of the following composition: 20 mM Tris-HCl, pH 7.5; 10 mM MgCl$_2$; 25 mM NaCl; 10 mM DTT; 1 mM ATP; 0.65 units (per well) Sequenase™; 0.4 units (per well) T4 DNA ligase.

In addition, some of the wells contained 30 µM biotin-14-dATP (obtained from GIBCO-BRL), and 30 µM of each of the three other dNTPs. Other wells contained 30 µM biotin-21-dUTP (obtained from Clontech) and 30 µM of the other three dNTPs. The extension-ligation reaction was allowed to proceed for 15 minutes at room temperature. The wells were washed with 1N NaOH and then incubated with a dilution of anti-biotin-horseradish peroxidase conjugate. After washing, the presence of the enzyme was detected using H$_2$O$_2$ and o-phenylenediamine hydrochloride, using a microplate reader in the kinetic mode. Wells containing biotinylated dTTP gave values of 168 mOD/min. Wells containing biotinylated dATP gave values of 7.8 mOD/min. Thus, the space between the two oligonucleotides has been filled with a labeled T, thereby identifying the opposite-strand base as an A.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method for determining the identity of nucleotide present at a preselected single nucleotide long site in a single-stranded target nucleic acid molecule, said method employing a set of oligonucleotides consisting of two oligonucleotides hybridizable to said target, and comprising the steps:

A) immobilizing a first oligonucleotide of said set of oligonucleotides, said first oligonucleotide being a primer oligonucleotide or a linker oligonucleotide, to a solid support; said first oligonucleotide having a nucleotide sequence complementary to, that of a first region of said target molecule, and being capable of hybridizing to said first region of said target molecule such that a terminus of said hybridized first oligonucleotide is immediately adjacent to said preselected site;

B) incubating said immobilized first oligonucleotide in the presence of said target molecule, and in the further presence of a labeled or unlabeled second oligonucleotide of said set of oligonucleotides, said second oligonucleotide being a primer oligonucleotide when said first oligonucleotide is a linker oligonucleotide or a linker oligonucleotide when said first oligonucleotide is a primer oligonucleotide; said second oligonucleotide having a sequence complementary to that of a second region of said target molecule, and being capable of hybridizing to said second region of said target molecule, wherein said first and second regions are separated from one another by said preselected site; said incubation being under conditions sufficient to permit said first and second oligonucleotides to hybridize to said target molecule to thereby form a hybridized product in which said first and second oligonucleotides are separated from one another by a space of a single nucleotide, said space being opposite to said preselected site;

C) further incubating said hybridized product, in the presence of a polymerase, a ligase, and a nucleoside triphosphate mixture containing a nucleoside triphosphate species that is complementary to the nucleotide of said preselected site and is detectably labeled if said second oligonucleotide is unlabeled, said mixture composed of one deoxynucleoside triphosphate species and three dideoxynucleoside triphosphate species, such that regardless of the identity of the nucleotide of said preselected site, a template-dependent, polymerase-mediated extension reaction will occur, causing a nucleoside triphosphate species of said nucleoside triphosphate mixture, complementary to that of the nucleotide of the preselected site, to become incorporated onto the 3' terminus of whichever of said first or said second oligonucleotide is the primer oligonucleotide; said incubation being under conditions sufficient to permit said template-dependent, polymerase mediated, incorporation to occur, and to thereby fill the space between said hybridized oligonucleotides and cause said oligonucleotides to abut;

D) permitting said ligase to ligate together abutting first and second hybridized oligonucleotides;

E) further incubating said immobilized first oligonucleotide under conditions sufficient to separate any non-covalently bonded target or second oligonucleotide therefrom; and F) determining whether said immobilized first oligonucleotide of step E has become labeled, wherein the presence of an immobilized labeled oligonucleotide indicates that the identity of said nucleotide of said preselected site is complementary to the deoxynucleoside triphosphate of said deoxynucleoside triphosphate mixture.

2. The method of claim 1, wherein said first and second oligonucleotides and said target molecule are DNA molecules.

3. The method of claim 1, wherein said first and second oligonucleotides and said target molecule are RNA molecules.

4. The method of claim 3, wherein said polymerase is reverse transcriptase and said ligase is RNA ligase.

5. The method of claim 2, wherein in step A, said first oligonucleotide is a linker oligonucleotide, and wherein the 3'-terminus of said first oligonucleotide is immobilized to said solid support, and wherein in step C, said conditions permit the incorporation of said nucleoside triphosphate onto the 3'-terminus of said second hybridized oligonucleotide, said second oligonucleotide being a primer oligonucleotide.

6. The method of claim 2, wherein step C, said nucleoside triphosphate mixture contains at least one detectably labeled deoxynucleoside triphosphate.

7. The method of claim 6, wherein said detectable label is an enzyme label, a fluorescent label, a radioisotopic label, or a chemiluminescent label.

8. The method of claim 6, wherein in step F, the identity of said nucleotide of said preselected site is determined by detecting the immobilized label of said nucleotide.

9. The method of claim 2, wherein said second oligonucleotide is a primer oligonucleotide, and wherein in step B, said second oligonucleotide is detectably labeled and all of the nucleoside triphosphates are unlabeled.

10. The method of claim 9, wherein said detectable label is an enzyme label, a fluorescent label, a radioisotopic label, or a chemiluminescent label.

11. The method of claim 9, wherein in step F, the identity of said nucleotide of said preselected site is deduced from the mixture of deoxynucleotide and dideoxynucleotide triphosphates used in step C.

12. The method of claim 1, wherein said first oligonucleotide is a primer oligonucleotide, and wherein in step A, the 5'-terminus of said first oligonucleotide is immobilized to said solid support, and wherein in step C, said conditions permit the incorporation of said nucleoside triphosphate onto the 3'-terminus of said immobilized oligonucleotide.

13. The method of claim 12, wherein said second oligonucleotide is a linker oligonucleotide, and wherein said second oligonucleotide is detectably labeled at its 3'-end.

14. The method of claim 13, wherein in step F, the identity of said nucleotide of said preselected site is deduced from the mixture of deoxynucleotide and dideoxynucleotide triphosphates used in step C.

15. The method of claim 1, wherein said target molecule contains a polymorphism, and said preselected site contains the variable nucleotide of said polymorphism.

16. The method of claim 15, wherein said target molecule is obtained from an animal selected from the group consisting of a horse, a sheep, a bovine, a canine, a feline, and a human.

17. The method of claim 15, wherein said target molecule is amplified in vitro from nucleic acid of an animal.

18. The method of claim 17, wherein said animal is selected from the group consisting of a horse, a sheep, a bovine, a canine, a feline, and a human.

19. The method of claim 15, wherein said target molecule is obtained from a plant.

20. The method of claim 15, wherein said target molecule is amplified in vitro from nucleic acid of a plant.

21. The method of claim 15, wherein said target molecule is obtained from a virus, a bacterium, a yeast or a fungi.

22. The method of claim 15, wherein said target molecule is amplified in vitro from nucleic acid of a virus, a bacterium, a yeast or a fungi.

23. A method for determining the identity of a nucleotide present at a preselected single nucleotide long site in a single-stranded target nucleic acid molecule, said method employing a set of oligonucleotides consisting of two oligonucleotides hybridizable to said target, and comprising the steps:

A) incubating said target molecule in the presence of a first oligonucleotide of said set of oligonucleotides, said first oligonucleotide being a primer oligonucleotide or a linker oligonucleotide, wherein said first oligonucleotide contains a bound ligand selected from the group consisting of biotin and fluorescein; said first oligonucleotide having a nucleotide sequence complementary to that of a first region of said target molecule, and being capable of hybridizing to said first region of said target molecule such that a terminus of said hybridized first oligonucleotide is immediately adjacent to said preselected site;

B) further incubating said provided first oligonucleotide and said target molecule in the presence of a labeled or unlabeled second oligonucleotide of said set of oligonucleotides, said second oligonucleotide being a primer oligonucleotide when said first oligonucleotide is a linker oligonucleotide or a linker oligonucleotide when said first oligonucleotide is a primer oligonucleotide; said second oligonucleotide having a sequence complementary to that of a second region of said target molecule, and being capable of hybridizing to said second region of said target molecule, wherein said first and second regions are separated from one another by said preselected site; said incubation being under conditions sufficient to permit said first and second oligonucleotides to hybridize to said target molecule to thereby form a hybridized product in which said first and second oligonucleotides are separated from one another by a space of a single nucleotide, said space being opposite to said preselected site;

C) further incubating said hybridized product, in the presence of a polymerase, a ligase, and a nucleoside triphosphate mixture containing a nucleoside triphosphate species that is complementary to the nucleotide of said preselected site and is detectably labeled if said second oligonucleotide is unlabeled, said mixture composed of one deoxynucleoside triphosphate species and three dideoxynucleoside triphosphate species, such that regardless of the identity of the nucleotide of said preselected site, a template-dependent, polymerase-mediated extension reaction will occur, causing a nucleoside triphosphate species of said nucleoside triphosphate mixture, complementary, to that of the nucleotide of the preselected site, to become incorporated onto the 3' terminus of whichever of said first or said second oligonucleotide is the primer oligonucleotide; said incubation being under conditions sufficient to permit said template-dependent, polymerase mediated, incorporation to occur, and to thereby fill the space between said hybridized oligonucleotides and cause said oligonucleotides to abut;

D) permitting said ligase to ligate together abutting first and second hybridized oligonucleotides to thereby form a first and second oligonucleotide ligation product;

E) capturing the first and second oligonucleotide ligation product onto a solid phase using the ligand and further incubating said provided first oligonucleotide under conditions sufficient to remove any non-covalently bonded target or second oligonucleotide from said incubation; and F) determining whether said immobilized first oligonucleotide of step E has become labeled, wherein the presence of an immobilized labeled oligonucleotide indicates that the identity of said nucleotide of said preselected site is complementary to the deoxynucleoside triphosphate of said deoxynucleoside triphosphate mixture.

24. A method for determining the identity of a nucleotide present at a preselected single nucleotide long site in a single-stranded target nucleic acid molecule, said method employing a set of oligonucleotides consisting of two oligonucleotides hybridizable to said target, and comprising the steps:

A) incubating said target molecule in the presence of a first oligonucleotide of said set of oligonucleotides, said first oligonucleotide being a primer oligonucleotide or a linker oligonucleotide, wherein said first oligonucleotide is labeled with a ligand selected from the group consisting of biotin and fluorescein; said first oligonucleotide having a nucleotide sequence complementary to that of a first region of said target molecule, and being capable of hybridizing to said first region of said target molecule such that a terminus of said hybridized first oligonucleotide is immediately adjacent to said preselected site;

B) further incubating said provided first oligonucleotide and said target molecule in the presence of a second oligonucleotide of said set of oligonucleotides, said second oligonucleotide being a primer oligonucleotide when said first oligonucleotide is a linker oligonucleotide or a linker oligonucleotide when said first oligonucleotide is a primer oligonucleotide; said second oligonucleotide having a sequence complementary to that of a second region of said target molecule, and being capable of hybridizing to said second region of said target molecule, wherein said first and second regions are separated from one another by said preselected site; said incubation being under conditions sufficient to permit said first and second oligonucleotides to hybridize to said target molecule to thereby form a hybridized product in which said first and second oligonucleotides are separated from one another by a space of a single nucleotide, said space being opposite to said preselected site;

C) further incubating said hybridized product, in the presence of a polymerase, a ligase, and a nucleoside triphosphate mixture containing a nucleoside triphosphate species that is complementary to the nucleotide of said preselected site and is detectably labeled if said second oligonucleotide is unlabeled, said mixture composed of one deoxynucleoside triphosphate species and three dideoxynucleoside triphosphate species, such that regardless of the identity of the nucleotide of said preselected site, a template-dependent, polymerase-mediated extension reaction will occur, causing a nucleoside triphosphate species of said nucleoside triphosphate mixture, complementary to that of the nucleotide of the preselected site, to become incorporated onto the 3' terminus of whichever of said first or said second oligonucleotide is the primer oligonucleotide; said incubation being under conditions sufficient to permit said template-dependent, polymerase mediated, incorporation to occur, and to thereby fill the space between said hybridized oligonucleotides and cause said oligonucleotides to abut;

D) permitting said ligase to ligate together abutting first and second hybridized oligonucleotides to thereby form a first and second oligonucleotide ligation product;

E) further incubating said provided first oligonucleotide under conditions sufficient to separate any non-covalently bonded target or second oligonucleotide therefrom and to retain the ligated oligonucleotides in solution;

F) determining whether said immobilized first oligonucleotide of step E has become labeled, wherein the presence of an immobilized labeled oligonucleotide indicates that the identity of said nucleotide of said preselected site is complementary to the deoxynucleoside triphosphate of said deoxynucleoside triphosphate mixture.

* * * * *

UNITED STATES PATENT AND TRADEMARK OFFICE
CERTIFICATE OF CORRECTION

PATENT NO : 5,679,524
DATED : October 21, 1997
INVENTOR(S): Nikiforov et al.

It is certified that error appears in the above-identified patent and that said Letters Patent is hereby corrected as shown below:

In Claim 24, Column 30, line 34, delete "immobilized"

In Claim 24, Column 30, line 36, delete "immobilized"

Signed and Sealed this

Twenty-ninth Day of May, 2001

Attest:

NICHOLAS P. GODICI

Attesting Officer

Acting Director of the United States Patent and Trademark Office